United States Patent [19]

McRae

[11] Patent Number: Plant 5,959

[45] Date of Patent: Apr. 28, 1987

[54] ASIATIC LILY NAMED ZEPHYR

[75] Inventor: Edward A. McRae, Boring, Oreg.

[73] Assignee: Melridge, Inc., Gresham, Oreg.

[21] Appl. No.: 710,578

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of hybrid Asiatic lily having flowers of excellent form and large size characterized by a clear medium pink color tone, which is fully unique in the upright Asiatic division of lilies, the flowers being borne in large, compact racemes comprising six to twelve flowers on a single stem. Also, this new plant is highly resistant to disease showing high tolerance to virus and is an excellent garden plant with bulbs that may be precooled and forced for cut-flower production.

1 Drawing Figure

BACKGROUND OF THE NEW PLANT

This new variety of lily plant originated as a seedling selected from my crossing a selected unnamed clone with the parentage Hallmark×"Destiny" and the cultivar "Sunrise" in the course of breeding efforts carried on by me at Sandy, Oreg., since the year 1972, the breeding efforts in this case having as their objective the production of superior upright-flowering Asiatic lilies in the shades of pink and suited to cut-flower production.

The flowers of my new lily plant are characterized by an exceptionally clear medium pink color tone, and in addition, the selected seedling appeared to possess the desirable characteristics of excellence of form, color, and habit to a high degree. This selected seedling was asexually reproduced by me and also under my direction at Sandy, Oreg., and successive generations of the new plant produced by bulb-scale propagation and natural propagation from bulblets demonstrate that the new plant possesses the desirable characteristics of hybrid vigor, great hardiness, and a high degree of disease resistance, as well as being a vigorous and good grower and propagator as observed in western Oregon. The successive asexual propagations of this new variety have also demonstrated that its desirable characteristics hold true from generation to generation and appear to be firmly fixed.

DESCRIPTION OF THE DRAWING

This new lily plant is illustrated in the accompanying photographic drawing which shows a three-quarter view of an open bloom and illustrates the flower form, tepal arrangement, and in particular, the novel and distinctive medium pink color tone of the entire bloom, which has been hand-painted thereon with the colors herein specified.

DESCRIPTION OF THE NEW VARIETY

The following is a detailed description of my new variety of Asiatic hybrid lily with color designations according to The R.H.S. Colour Chart published by The Royal Horticultural Society of London, England, and with nomenclature according to The International Lily Register of The Royal Horticultural Society.

THE PLANT

Origin: Seedling.

Parentage:

*Seed parent.*—An unnamed selected clone of Hallmark×"Destiny" (unpatented).

*Pollen parent.*—"Sunrise" (unpatented).

Classification:

*Horticultural.*—Hybrid lily cultivar, Division I-A of the Horticultural Classification of Lilies by The Royal Horticultural Society.

*Commercial.*—Upright Asiatic hybrid lily.

Form: Single stem, erect, and stately.

Height: about 90 to 130 cm. from bulbs about 12 to 15 cm. in circumference.

Growth: Vigorous, sturdy, and upright.

Foliage:

*Quantity.*—Abundant.

*Leaf size.*—About 10 to 12 cm. long and about 1.0 cm. wide at the base.

*Leaf shape.*—Sessile lanceolate.
*Texture.*—Leathery with lightly pubescent margins.
*Aspect.*—Glossy.
*Color.*—Light to medium green.

Bulbs:
*Size.* Ranging up to 25 cm. in circumference in commercial use.
*Color.*—White.

THE BUD

Form: Long ovoid with obtuse ends.
Size: About 7 to 9 cm. long just prior to opening.
Opening rate: The bud opens slowly at maturity, in response to light.
Color: Medium to soft clear Pink, RHS 62, when the outer petals first divide and when the tepals begin to unfurl.
Peduncle:
*Length.*—About 7 to 10 cm., depending upon light levels.
*Color.*—Light green.

THE FLOWER

Blooming habit: Annually, once and profusely in mid-season for Asiatic lilies. October-dug bulbs, properly precooled and planted under glass in western Oregon, with no supplementary lighting, flower in an average of about 90 days when grown at moderate temperatures.
Size: Medium to large; about 14 to 18 cm. in diameter.
Borne: As a compact raceme with 6 to about 12 blossoms on a single stem.
Shape: Generally dish-shaped to flat.
Tepalage:
*Number.*—Six.
*Arrangement.*—The petals overlap the sepals midway between them.
*Color.*—Clear medium Pink, RHS 62B, shading to a slightly lighter color tone, RHS 62C, near the base of the tepals.
*Spotting.*—A moderate number of tiny dark magenta-pigmented spots cover the inner halves of the tepals.
*Color change.*—The pink color may deepen slightly as the flower ages if adequate light levels and cool temperatures are maintained.
*Tepal longevity.*—Tepals stay on the stem about three weeks.

Fragrance: None.
Disease resistance: Both flower and plant are resistant to disease, and are particularly resistant to Fusarium and Botrytis.
Lasting quality: The flower is long lasting, both on the plant and as a cut flower.

REPRODUCTIVE ORGANS

Stamens:
*Number.*—Six.
*Arrangement.*—Typical of genus Lilium.
Anthers:
*Color.*—Greyed gold.
Filaments:
*Length.*—About 5 cm.
*Color.*—Ivory or soft pink.
Pollen:
*Color.*—Same as anthers.
Pistils:
*Number.*—One.
Style:
*Length.*—About 5 cm.
Stigma:
*Color.*—Light to deep plum.
Character of ovary: Typical of genus Lilium.

THE FRUIT

Fertility: The fruit is fertile.
Shape: Ovoid.
Color at maturity: Soft brown, sometimes overlaid with light plum.

My herein described variety of Asiatic lily most nearly resembles the cultivar "Sunrise" (unpatented) but it differs by having upright flowers rather than side-facing flowers and a clear medium pink color rather than the pink-tipped white flowers of "Sunrise". Also, the new plant is much taller than "Sunrise".

I claim:

1. A new and distinctive variety of Asiatic hybrid lily plant, substantially as herein shown and described, characterized by its unique clear medium pink color tone and the excellence of its flower form and substance, its versatility both as a garden plant and as a plant produced from precooled bulbs forced for cut-flower production, and its high resistance to disease and tolerance to virus.

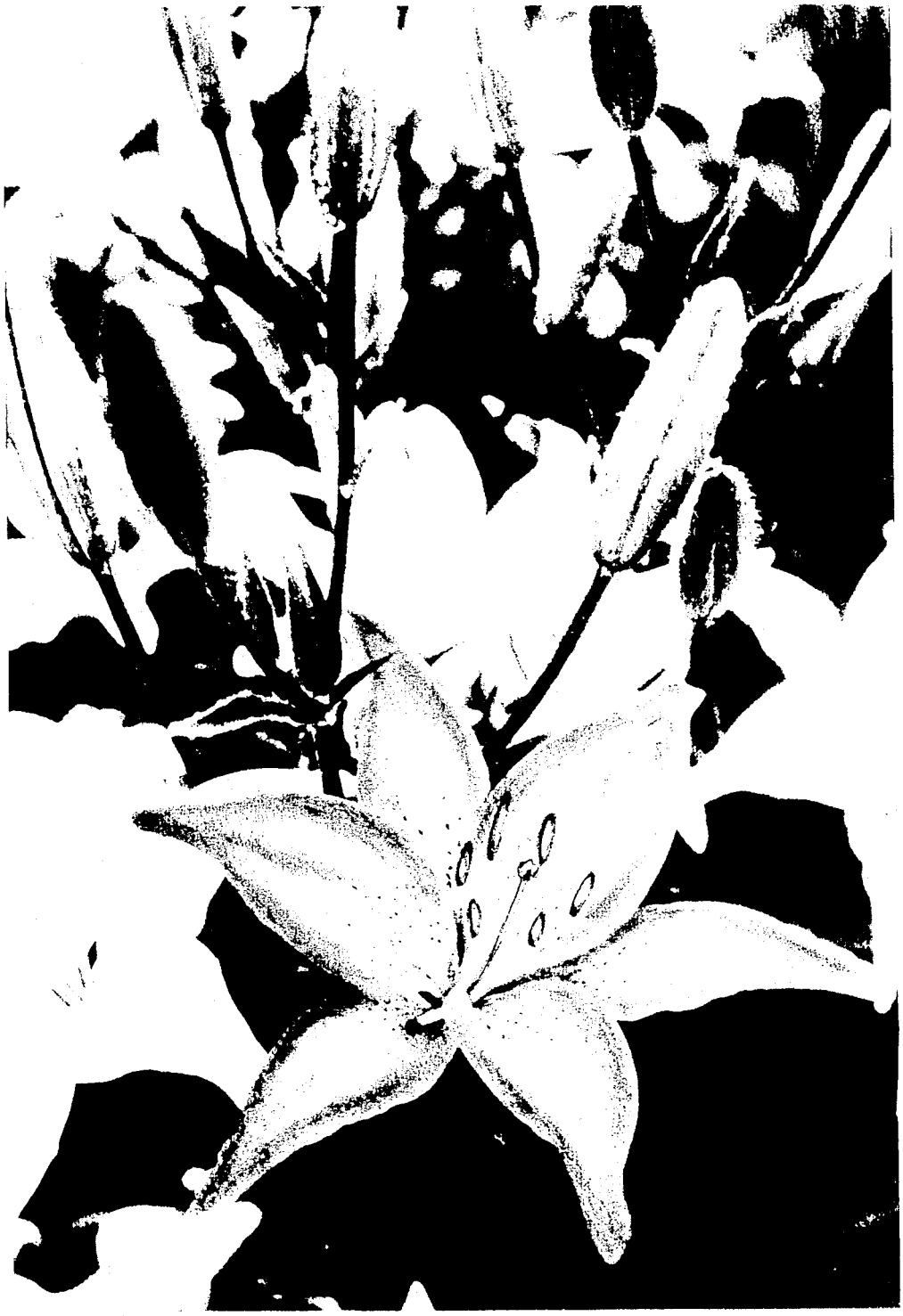

* * * * *